(12) United States Patent
Zhang et al.

(10) Patent No.: US 7,531,698 B2
(45) Date of Patent: May 12, 2009

(54) TETRAPHOSPHORUS LIGANDS FOR CATALYTIC HYDROFORMYLATION AND RELATED REACTIONS

(75) Inventors: Xumu Zhang, State College, PA (US); Yongjun Yan, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 120 days.

(21) Appl. No.: 11/639,438

(22) Filed: Dec. 15, 2006

(65) Prior Publication Data

US 2007/0203365 A1 Aug. 30, 2007

Related U.S. Application Data

(60) Provisional application No. 60/750,733, filed on Dec. 15, 2005.

(51) Int. Cl.
C07C 45/00 (2006.01)
(52) U.S. Cl. .............. 568/455; 568/8; 568/10; 568/25; 568/300; 558/335; 558/332; 556/14; 502/502; 548/162
(58) Field of Classification Search .......... 568/455, 568/25, 8, 10, 300; 548/412; 558/335, 332; 556/14; 502/162
See application file for complete search history.

(56) References Cited

U.S. PATENT DOCUMENTS 3,420,864 A * 1/1969 Riess et al. ............... 556/16
6,437,192 B1 * 8/2002 Bunel ....................... 568/454
6,846,945 B2 * 1/2005 Lenges et al. ............. 558/335

OTHER PUBLICATIONS

Agranat et al., Multiple Horner-Emmons cyclizations as a route to nonbenzenoid aromatics. Synthesis of polycyclic dodecalenes, Journal of Organic Chemistry (1979), 44(12), 1936-1941.*

Agranat et al., {Multiple Horner-Emmons cyclizations as a route to nonbenzenoid aromatics. Synthesis of polycyclic dodecalenes, Journal of Organic Chemistry (1979), 44(12), 1936-1941}.*
Dai, Q., et al., "Triazole-Based Monophosphine Ligands for Palladium-Catalyzed Cross-Coupling Reactions of Aryl Chlorides," The Journal of Organic Chemistry, May 12, 2006, pp 3928-3934, vol. 71, No. 10, American Chemical Society, Washington, D.C.
Liu, D., et al., "Triazole-Based Monophosphines for Suzuki-Miyaura Coupling and Amination Reactions of Aryl Chlorides," Organic Letters, 2005, pp. 4907-4910, vol. 7, No. 22, American Chemical Society, Washington, D.C.
International Search Report and Written Opinion of the International Searching Authority, issued in corresponding International Application No. PCT/US06/47766, dated on Oct. 2, 2007.
Supplemental European Search Report and Written Opinion issued in European Patent Application No. EP 6845453.7 dated on Jan. 23, 2009.
Van Der Slot et al "Rhodium-Catalyzed Hydroformylation and Deuteriorformylation with Pyrrolyl Based Phosphorus Amidite Ligands: Influence of Electronic Ligan Properites" Organometallics pp. 3873-3883 The American Chemical Society 2002.
Kunze Synthesis of New Calix[4]arene-Based Phosphorus Ligands and Their Application in the Rh(I) Catalyzed Hydroformylation of 1-Octene pp. 577-585 Heroatom Chemistry vol. 12, No. 7 2001.
Aikawa et al "Atropos but Achiral Tris(phosphanyl)biphenyl Ligands for Ru-Catalyzed Asymmetric Hydrogenation" Communications pp. 5455-5458 Angewandte Chemistry 2003.
Paciello et al "Structure-activity relationship for chelating phosphate ligands used in rhodium-catalyzed hydroformylations" pp. 85-97 Journal of Molecular catalysis A Chemical vol. 143 1999 Elzevier, www. Elsevier.com/locate/molcata.
Yan et al "Tetraphosphorous Ligand for Highly Regioselective Isomerization-Hydroformylation of Internal Olefins" pp. 16508-16061 Journal of American Chemical Society 2006 published on web Dec. 24, 2006.

* cited by examiner

*Primary Examiner*—Sikarl A. Witherspoon
*Assistant Examiner*—Chukwuma O Nwaonicha
(74) *Attorney, Agent, or Firm*—McDermott Will & Emery LLP

(57) ABSTRACT

Tetraphosphorous ligands are combined with transition metal salts to form catalysts for use in hydroformylation, isomerization-hydroformylation, hydrocarboxylation, hydrocyanation, isomerization-formylation, hydroaminomethylation and similar related reactions.

8 Claims, No Drawings

TETRAPHOSPHORUS LIGANDS FOR CATALYTIC HYDROFORMYLATION AND RELATED REACTIONS

CROSS REFERENCE TO RELATED APPLICATION

This application claims the benefit of priority of Provisional Application No. 60/750,733 filed Dec. 15, 2005, which is incorporated herein by reference.

FIELD OF THE INVENTION

The present invention relates to new phosphorous ligands and their applications in hydroformylation and related reactions. More particularly, the present invention relates to transition metal complexes having chelating tetraphosphorus ligands with multichelating modes. Tetraphosphorus ligands with multichelating modes can enhance coordinating abilities for transition metals such as Rh and Ni, and thus enhance selectivities of catalytic reactions. The transition metal-tetraphosphorus complexes according to the present invention are useful as catalysts in hydroformylation, isomerization-hydroformylation, hydrocarboxylation, hydrocyanation, tandem reactions such as isomerization-formylation, and hydroaminomethylation.

BACKGROUND OF THE INVENTION

Hydroformylation, discovered by Roelen in 1938, has been the largest homogeneous catalytic process in industry. More than 15 billion pounds of aldehydes and alcohols per year have been produced based on Fe, Zn, Mn, Co, Cu, Ag, Ni, Pt, Pd, Rh, Ru and Ir based catalysts. In these processes, achieving high selectivity to linear products is extremely important for commercial application. Despite the extensive investigation by both academic and industrial groups such as BASF, Dow, Shell and Eastman, among others, there still remain fundamental and practical problems regarding selectivity. New concepts for controlling selectivities are very important in catalytic reactions. Highly efficient selective catalysts will allow some bulky chemicals to be produced in an environmentally sound manner under milder conditions.

Cobalt catalysts (e.g., $HCo(CO)_4$) dominated industrial hydroformylation until rhodium catalysts (e.g., $HRh(CO)_2(PPh_3)_3$) were introduced in earlier 1970's. In 2004, it is estimated that approximately 75% of all hydroformylation processes were based on rhodium triarylphosphine catalysts. Achieving high regioselectivity to linear aldehydes is critical for hydroformylation and related reactions. The resulting aldehydes are converted to alcohols, carboxylic acids or other derivatives, which are used as plasticizers, detergents, surfactants, solvents, lubricants and chemical intermediates.

Scheme 1 below shows the dissociation of a Rh catalyzed hydroformylation catalyst.

The successful commercialization of $HRh(CO)(PPh_3)_2$ technology has been based on the key discovery of Pruett at Union Carbide and Booth at Union oil that the use of rhodium with excess phosphine ligand can lead to forming active, selective hydroformylation catalysts. The need for excess phosphines is due to the facile $Rh-PPh_3$ dissociation in the catalytic system as illustrated by Scheme 1. Loss of $PPh_3$ from $HRh(CO)(PPh_3)_2$ results in more active, but less regioselective hydroformylation catalysts B and C. In the commercial process, up to an 820 fold excess of $PPh_3$ to Rh is used to assure high linear:branch selectivity ratio, i.e., up to 17:1, for the hydroformylation of 1-hexene. Commercial hydroformylation of propylene has been run with a 400 fold excess of $PPh_3$ to Rh with a linear:branch selectivity ratio of 8-9:1 being achieved.

$Rh/PPh_3$ catalyzed hydroformylation is the key for making all oxo alcohols. Propylene is the largest single alkene hydroformylated to produce butylaldehyde, which can be hydrogenated to produce butanol, or dimerized by an aldol condensation and then hydrogenated to form 2-ethyl-1-hexanol, the largest single product produced by hydroformylation (over 5 billion lbs a year). 2-ethyl-1-hexanol is usually reacted with phthalic anhydride to produce dialkyl phthalic esters that are used as plasticizers to keep polyvinyl chloride plastics soft and flexible.

In the hydroformylation process, it is critical to get cheaper feed stocks for starting materials. For example, internal higher alkenes (SHOP alkenes) such as 3-octenes are desirable for converting the alkenes to linear aldehydes. Direct use of raffinate II (a mixture of n-butenes/butanes) and 1-butene and 2-butene mixtures are useful for hydroformylation. For hydroformylation of n-alkenes, it is important to obtain high linear selectivity. Hydroformylation of allylic alcohol and subsequent reduction can lead to 1, 4 butenol. Functionalized internal alkenes can be used as alternative routes to bifunctional building blocks for polymers. Hydroformylation of methyl-3-pentenoate leads to making starting materials for polyamides and polyesters. In the tandem-isomerization and hydroformylation processes, high isomerization rates combined with high selectivity towards terminal aldehydes are desirable with minimized undesirable hydrogenation reactions and minimiun isomerization towards conjugated compounds.

To overcome the need of using large excess of phosphines in the hydroformylation processes and achieve high regioselectivity, a new generation of transition metal catalysts were developed using bisphosphine ligands. For example: Bisbi by Eastman Chemical; Xantphos by Prof. Leeuwen (University of Amsterdam), Bernhard Breit, Acc. Chem. Res. 2003, 36, 264-275, Bernhard Breit, Wolfgang Seiche, Synthesis 2001, 1, 1-36); and UC-44 by Union Carbide. These ligands are illustrated below.

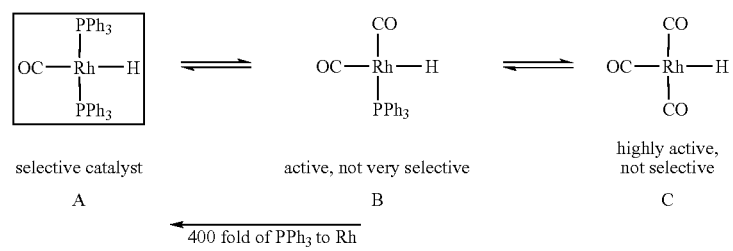

selective catalyst     active, not very selective     highly active, not selective

A     B     C 400 fold of $PPh_3$ to Rh

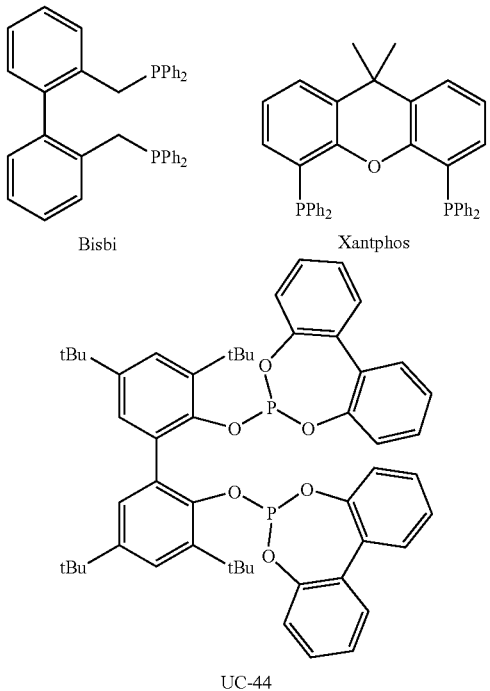

UC-44

By using these ligands, a typical 400 fold excess of $PPh_3$ has been reduced to a 5 fold excess of chelating phosphines. This new generation of chelating phosphines has led to high linear: branched ratios as well as to higher catalytic activities. For example, a linear to branch ratio of 70-120:1 for hydroformylation of 1-hexene has been observed. Casey and van Leeuwen proposed that part of regioselectivity in the Rh-catalyzed hydroformylation is due to metal bisphosphine bite angle around 120 degree is formed, i.e., "the Bite angle hypothesis" as illustrated below.

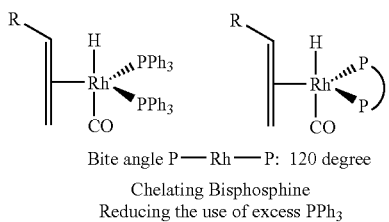

Bite angle P—Rh—P: 120 degree
Chelating Bisphosphine
Reducing the use of excess $PPh_3$ Despite that a number of chiral bisphosphorus ligands being used as catalysts for hydroformylation and related reactions, the highly selective, active phosphorus ligands for hydroformylation still remain an area of strong research interest. However, because of the dissociation of phosphines from the Rh—CO coordination, is a problem for achieving high regioselectivity, that is high linear to branch ratios of the products produced. Developing families of phosphorus ligands with multi-chelating coordination modes is attractive. The tetraphosphorous ligands of the present invention, because of their coordinating abilities through multi-chelating coordination modes, lead to highly regioselective transition in metal-ligand catalyzed hydroformylation and related reactions to provide high linear to branch ratios than those previously obtained. Also, the symmetric nature of these ligands allows these ligands to be prepared easily.

SUMMARY OF THE INVENTION

In the present invention, we introduce a variety of tetraphosphorus ligands (Type A) with multi-chelating coordination modes as illustrated below to enhance coordination abilities:

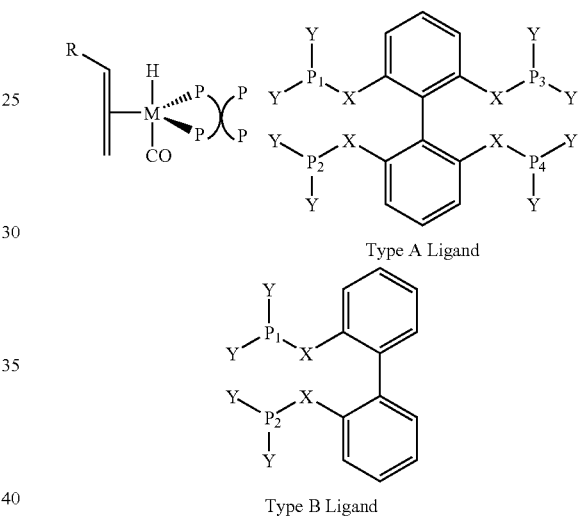

where M is a metal selected from the group consisting of Fe, Zn, Mn, Co, Cu, Ag, Ni, Pt, Pd, Rh, Ru and Ir; X is selected from the group consisting of O, NH, NR and $CH_2$; Y is selected from the group consisting of Ar, OAr and pyrrole; R is an organic group and Ar is an aryl group. Type A ligand is a tetraphosphorous ligand of the present invention. Type B ligand is a bisphosphorous ligand. As illustrated below, the tetraphosphorus ligand (Type A) has at least four chelating coordination modes to enhance coordination abilities whereas the bisphosphorus ligand (Type B) has a single mode, namely, $P_1$-M-$P_2$.

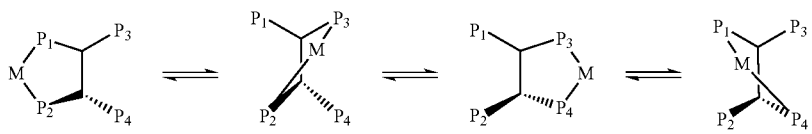

Compared with normal bisphosphorus ligands (Type B), the multi-chelating tetraphosphorus. ligands (Type A) of the present invention enhance the coordinating abilities of ligands without major change of electronic properties of ligands.

DETAILED DESCRIPTION OF THE INVENTION

The present invention is directed to tetraphosphorous ligands having multi-chelating coordination modes to used as catalysts for hydroformylation and related reactions. The transition metal catalysts prepared using the tetraphosphorous ligands of the present invention are highly active and regioselective. The tetraphosphorous ligands of the present invention have the following generic structure:

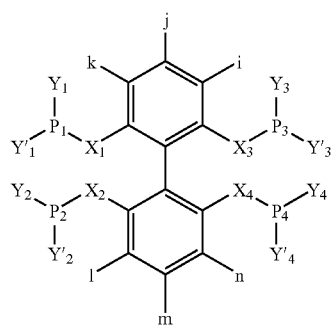

wherein i, j, k, l, m and n are, independently, H, R, Ar, substituted Ar, OR, OAr, COOEt, halide, SO$_2$R, SO$_3$H, SO$_2$NHR, POR$_2$, POAr$_2$ or NR$_2$, where R is an alkyl, substituted alkyl, aryl or substituted aryl and Ar is an aryl; X$_1$-X$_4$ are, independently, R, Ar, OR, OAr, pyrrole or substituted pyrrole, where R is an alkyl, substituted alkyl, aryl or substituted aryl and Ar is an aryl; and Y$_1$, Y'$_1$, Y$_2$, Y'$_2$, Y$_3$, Y'$_3$, Y$_4$, Y'$_4$, are, independently, R, Ar, OR, OAr, pyrrole or substituted pyrrole, where R is an alkyl, substituted alkyl, aryl or substituted aryl and Ar is an aryl, or where R, Ar, OR, OAr, pyrrole and substituted pyrrole are linked with a carbon to carbon bond, CH$_2$, NH, NR and O. The substituted groups would include, for example, methyl, ethyl, t-butyl and phenyl.

The following illustrates a first embodiment of the invention:

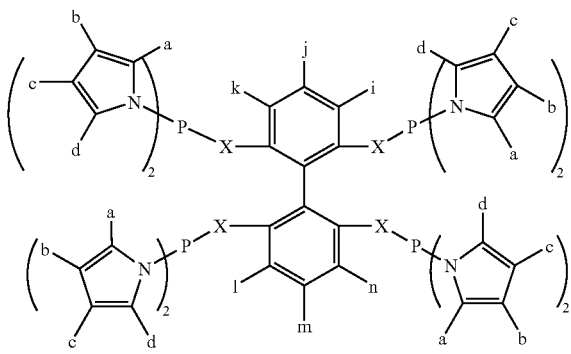

wherein X is O, CH$_2$, NH, NR, NSO$_2$R or NSO$_2$Ar, where R is an alkyl, substituted alkyl, aryl or substituted aryl and Ar is an aryl; and a, b c, d, i, j, k, l, m and n are, independently, H, alkyl, aryl, substituted alkyl, substituted aryl, OR, OAr, SiR$_3$, CF$_3$, COOR, SO$_3$R, SO$_3$H, POR$_2$, halide or two of a, b, c, d, i, j, k, l, m and n can be a cyclic fused ring or an extended aromatic ring, where R is an alkyl, substituted alkyl, aryl or substituted aryl and Ar is an aryl.

A second embodiment of the invention is illustrated below:

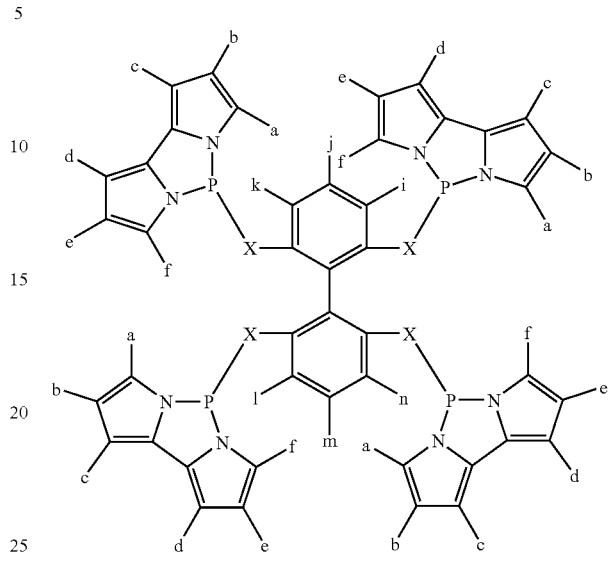

wherein X is O, CH$_2$, NH, NR, NSO$_2$R or NSO$_2$Ar, where R is an alkyl, substituted alkyl, aryl or substituted aryl; and Ar is an aryl; and a, b, c, d, e, f, i, j, k, l, m and n are, independently, H, alkyl, aryl, substituted alkyl, substituted aryl, OR, OAr, SiR$_3$, COOR, SO$_3$R, SO$_3$H, POR$_2$, halide or two of a, b, c, d, e, f, i, j, k, l, m and n can be a cyclic fused ring or an extended aromatic ring, where R is an alkyl, substituted alkyl, aryl or substituted aryl and Ar is an aryl.

A third embodiment of the invention is illustrated below:

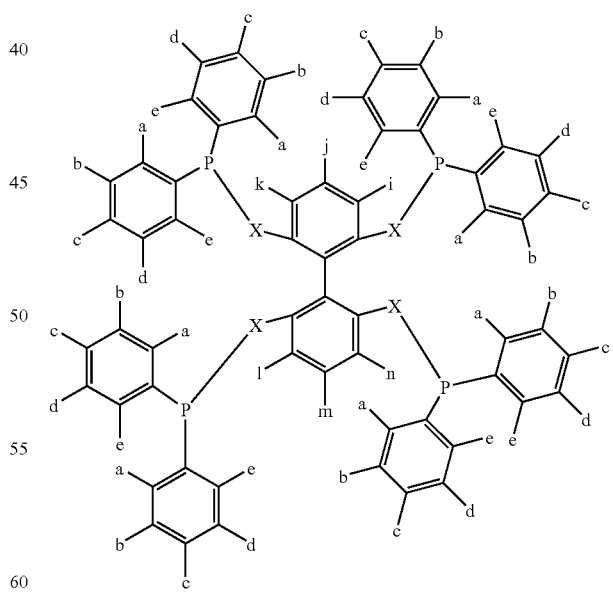

wherein X is O, CH$_2$, NH, NR, NSO$_2$R or NSO$_2$Ar, where R is an alkyl, substituted alkyl, aryl or substituted aryl and Ar is an aryl; and a, b, c, d, e, i, j, k, l, m and n are, independently, H, alkyl, aryl, substituted alkyl, substituted aryl, OR, OAr, SiR$_3$, CF$_3$, COOR, SO$_3$R, SO$_3$H, POR$_2$, halide, NR$_2$, or two of a, b, c, d, e, i, j, k, l, m and n can be a cyclic fused ring or an extended aromatic ring, where R is an alkyl, substituted alkyl, aryl or substituted aryl and Ar is an aryl.

A fourth embodiment of the invention is illustrated below:

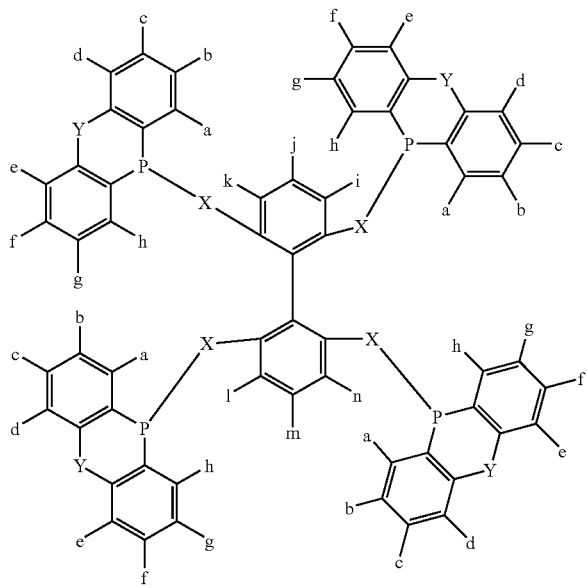

wherein X is O, $CH_2$, NH, NR, $NSO_2R$ or $NSO_2Ar$, where R is an alkyl, substituted alkyl, aryl or substituted aryl and Ar is an aryl; Y is a carbon-carbon bond, O, $CH_2$, NH or NR, where R is an alkyl, substituted alkyl, aryl or substituted aryl; and a to n are, independently, H, alkyl, aryl, substituted alkyl, substituted aryl, OR, OAr, $SiR_3$, $CF_3$, COOR, $SO_3R$, $SO_3H$, $POR_2$, halide, $NR_2$, or two of a to n can be a cyclic fused ring or an extended aromatic ring, where R is an alkyl, substituted alkyl, aryl or substituted aryl and Ar is an aryl.

A fifth embodiment of the invention is illustrated below:

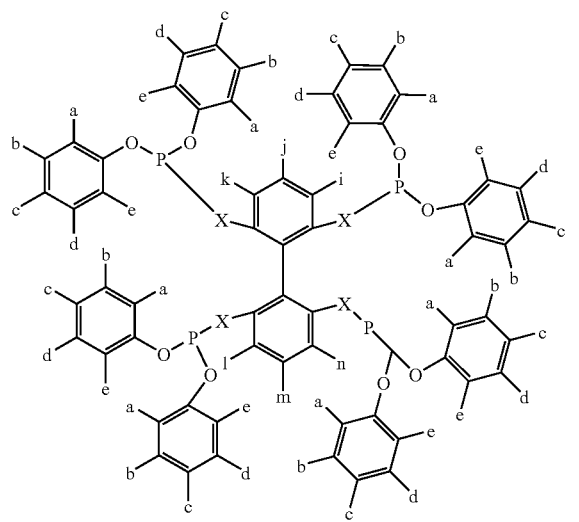

wherein X is O, $CH_2$, NH, NR, $NSO_2R$, or $NSO_2Ar$, where R is an alkyl, substituted alkyl, aryl or substituted aryl and Ar is an aryl; and a, b, c, d, e, i, j, k, l, m and n are, independently, H, alkyl, aryl, substituted alkyl, substituted aryl, OR, OAr, $SiR_3$, $CF_3$, COOR, $SO_3R$, $SO_3H$, $POR_2$, halide, $NR_2$, or two of a, b, c, d, e, i, j, k, l, m and n can be a cyclic fused ring or an extended aromatic ring, where R is an alkyl, substituted alkyl, aryl or substituted aryl and Ar is an aryl.

A sixth embodiment of the invention is illustrated below:

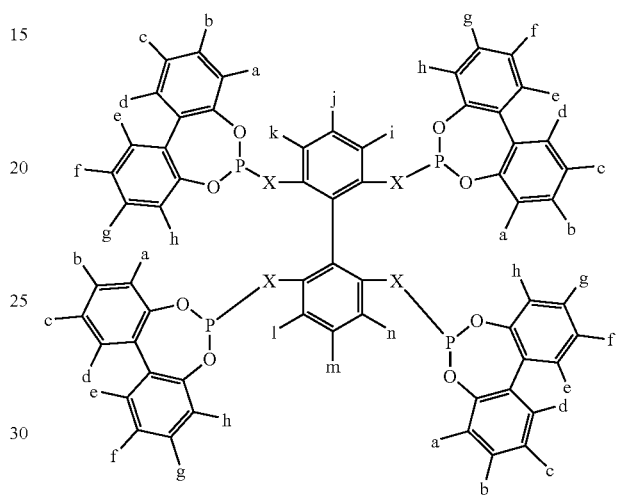

wherein X is O, $CH_2$, NH, NR, $NSO_2R$ or $NSO_2Ar$, where R is an alkyl, substituted alkyl, aryl or substituted aryl and Ar is an aryl; and a to n are, independently, H, alkyl, aryl, substituted alkyl, substituted aryl, OR, OAr, $SiR_3$, $CF_3$, COOR, $SO_3R$, $SO_3H$, $POR_2$, halide, $NR_2$, or two of a to n can be a cyclic fused ring or an extended aromatic ring, where R is an alkyl, substituted alkyl, aryl or substituted aryl and Ar is an aryl. When d and e are not hydrogen, enantiomers of these ligands can prepared for asymmetric catalytic reactions.

Examples of the tetraphosphorus ligands of the present invention (L1 to L91) are illustrated below:

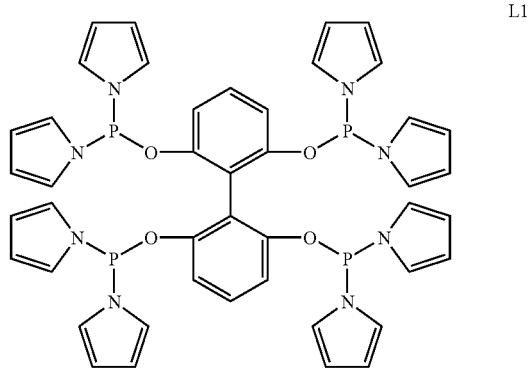

L1

-continued
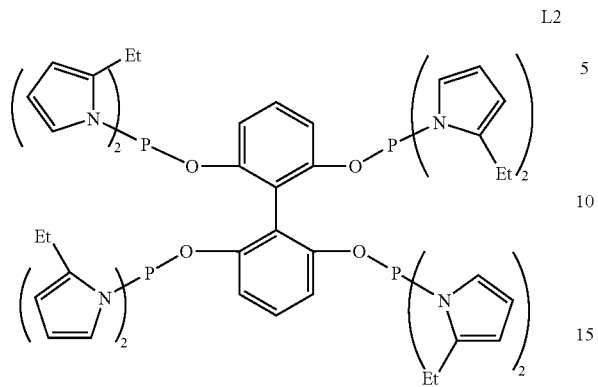
L2
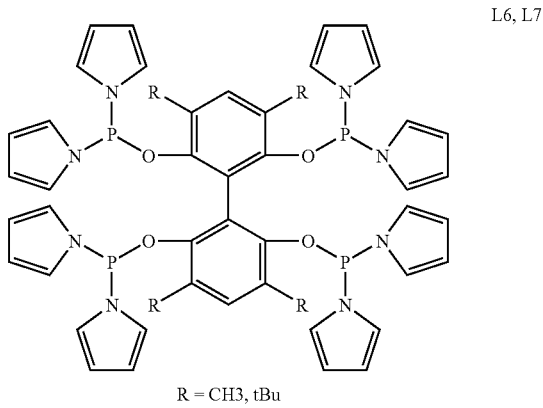
L6, L7
R = CH3, tBu
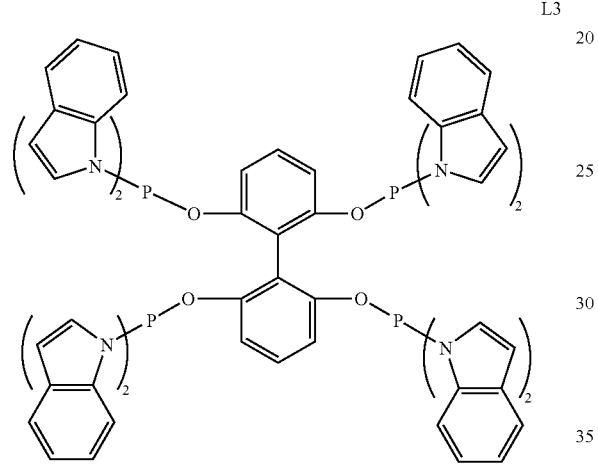
L3
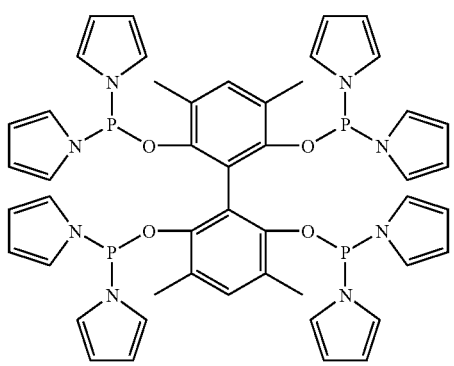
L8
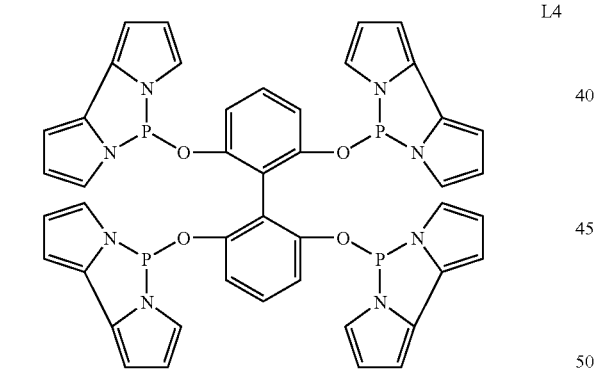
L4
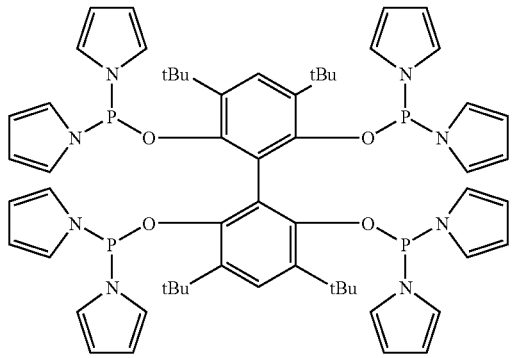
L9
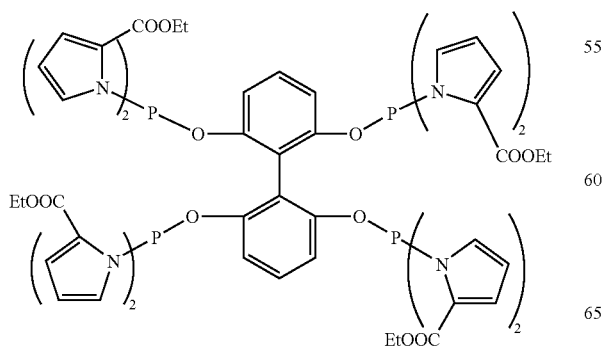
L5
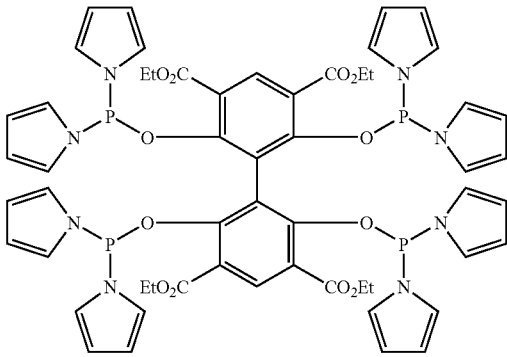
L10

-continued
L11
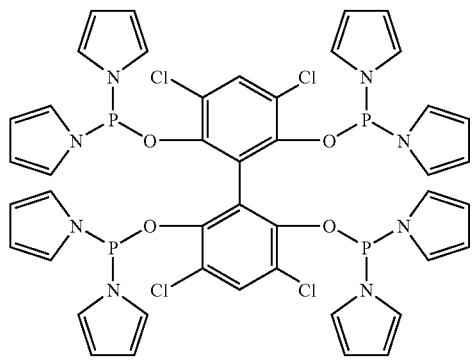
L12
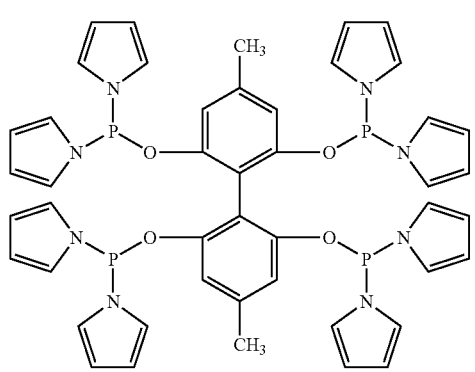
L13
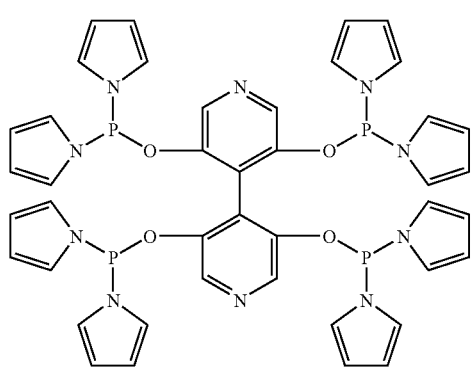
L14
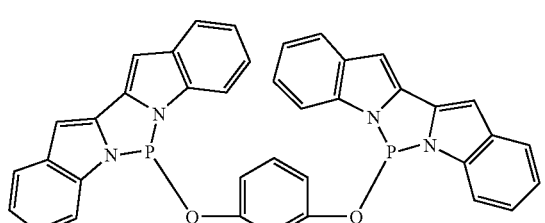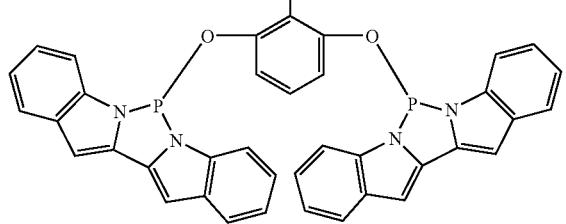
-continued
L15
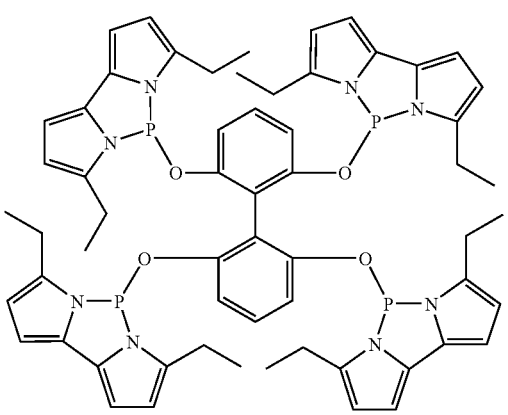
L16
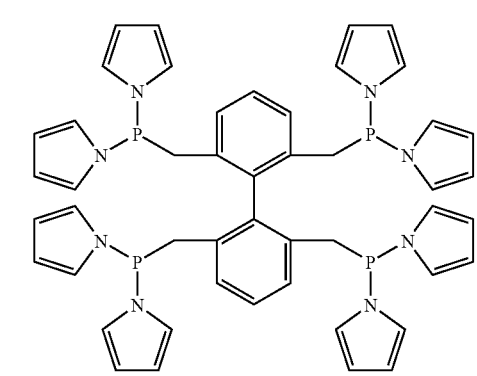
L17
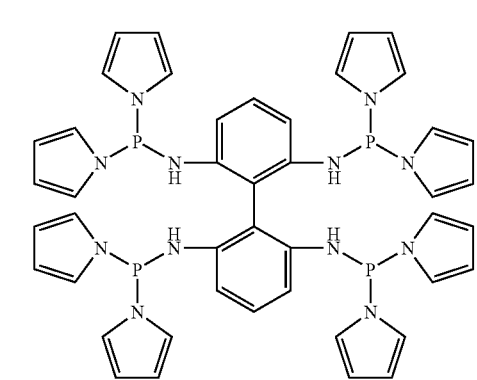
L18
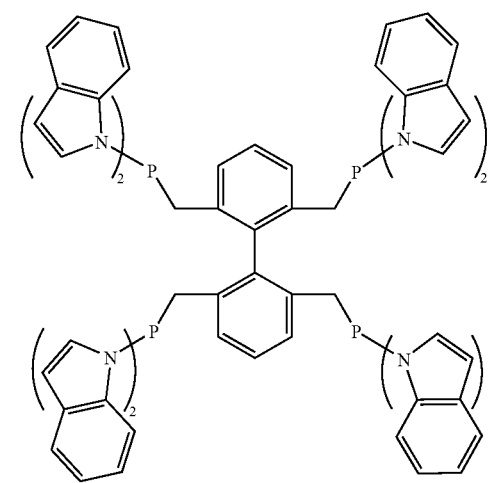

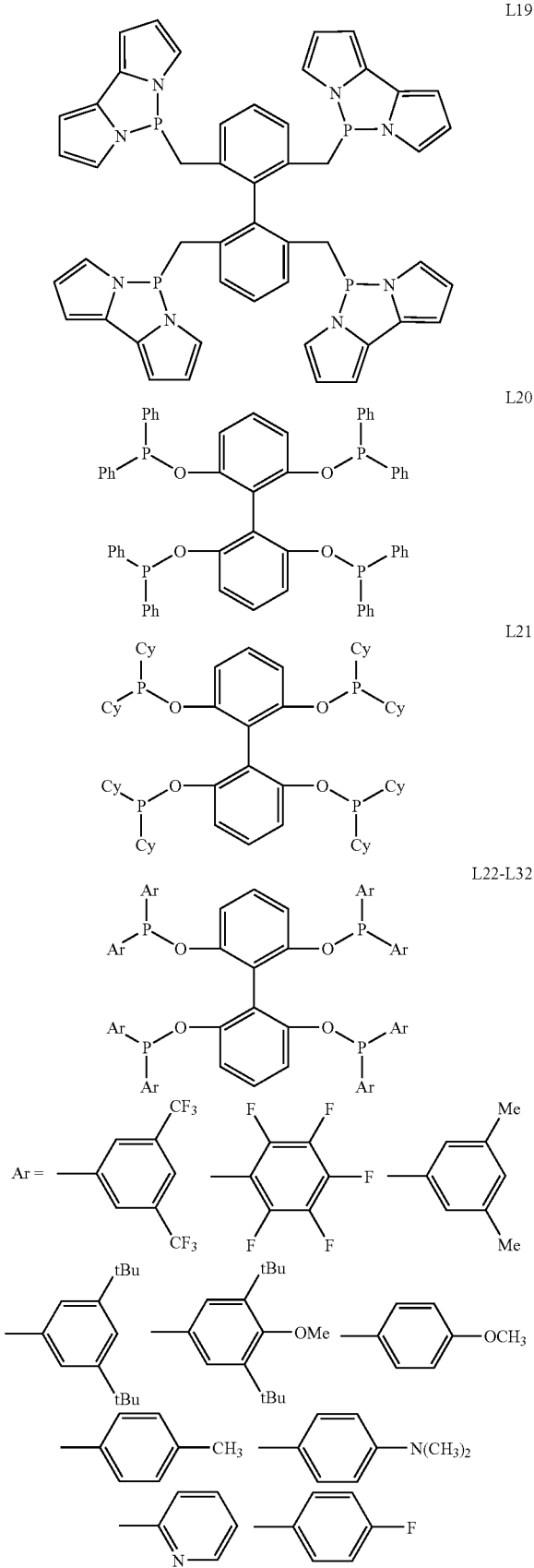
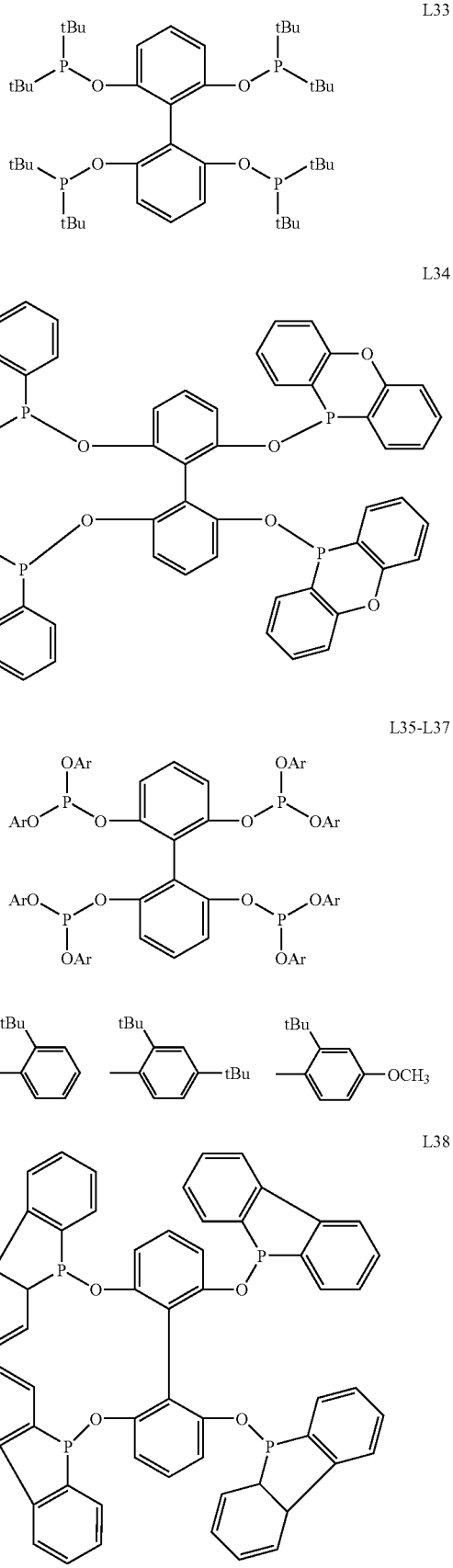

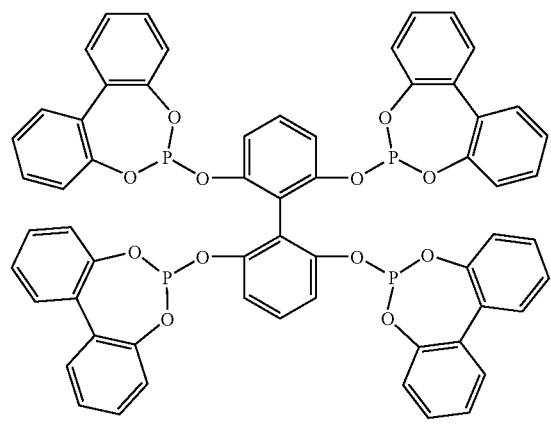
L39
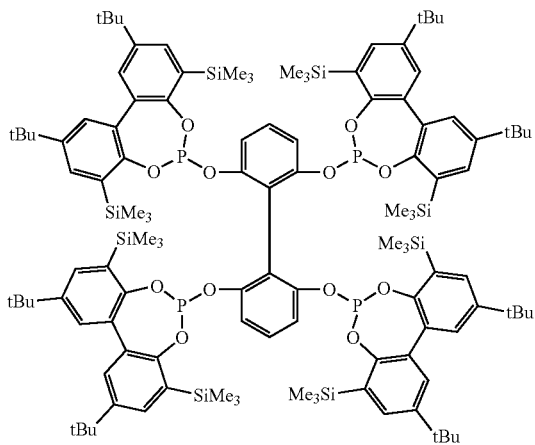
L42
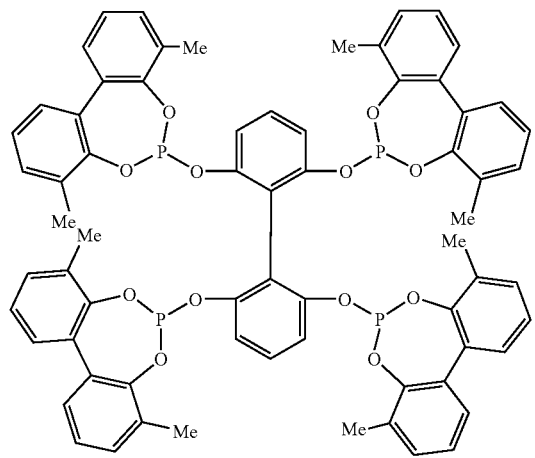
L43
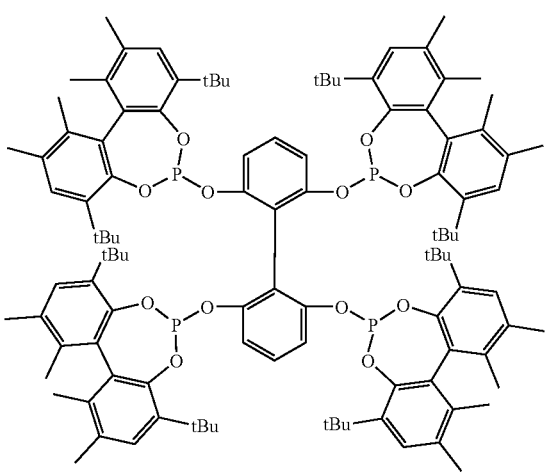
L44

-continued
L45
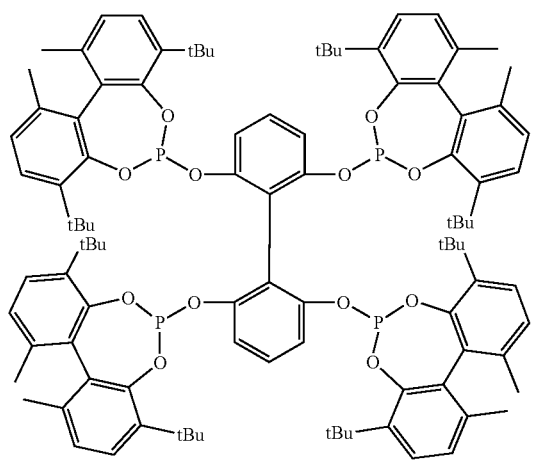
L46-L53
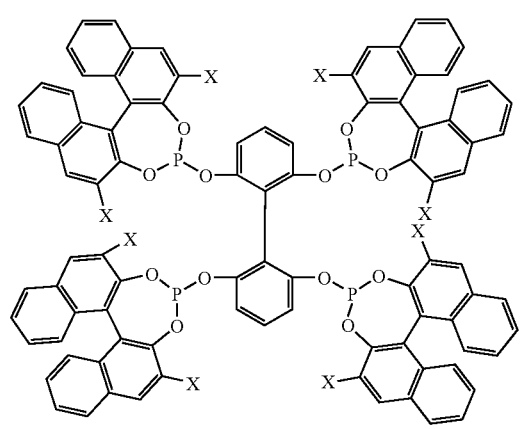
X = H, SiME₃, Br, I, COOEt, CF₃, Ph, substituted aryl
L54
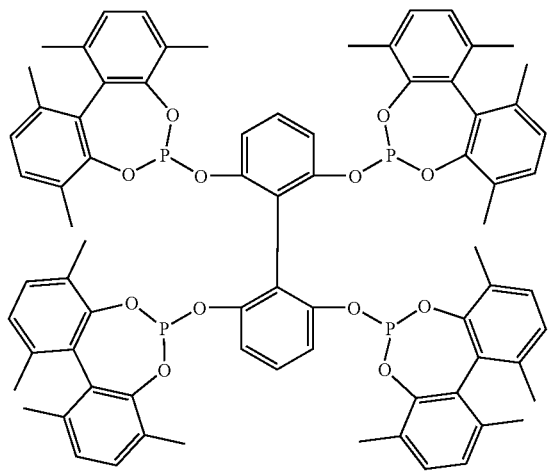
-continued
L55
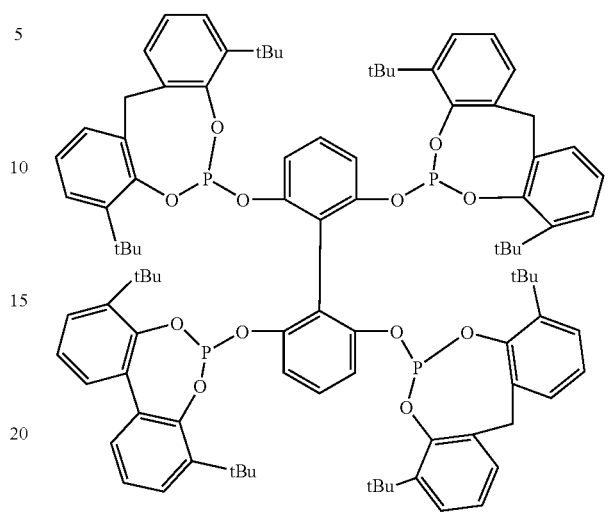
L56-L58
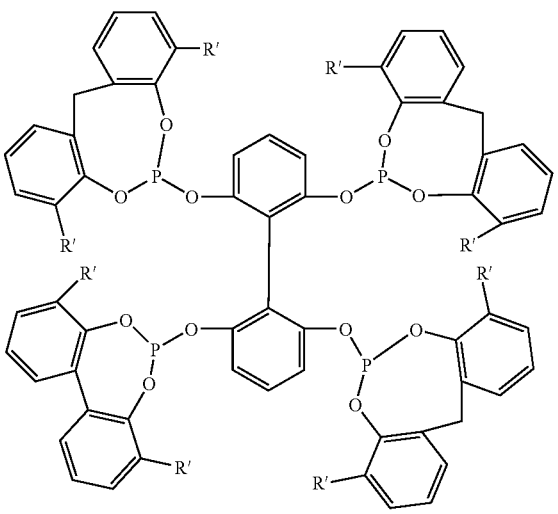
R' = H, alkyl, aryl
L59-L62
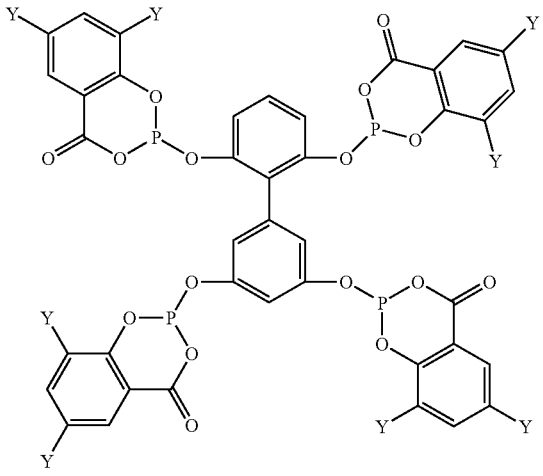
Y = Br, Me, iPr, tBu R' = H, alkyl, aryl, Y = Br, Me, iPr, tBu

L87

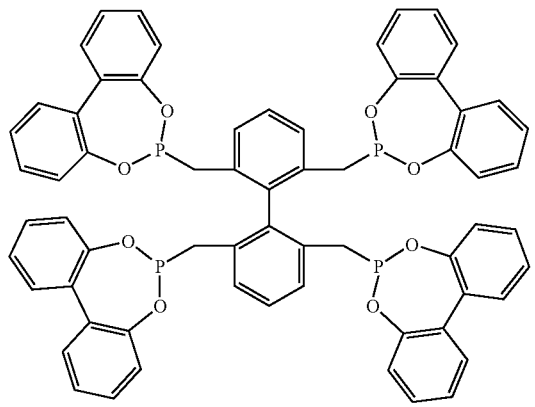

L88

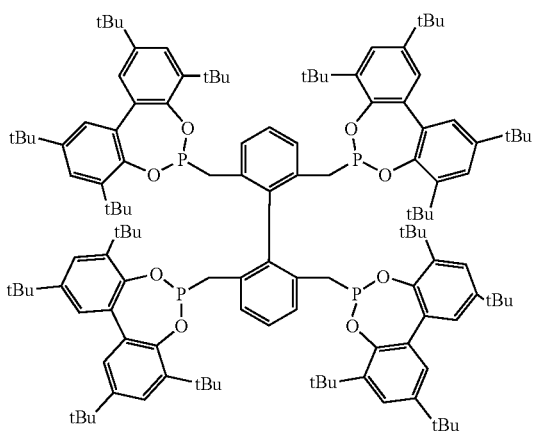

L89

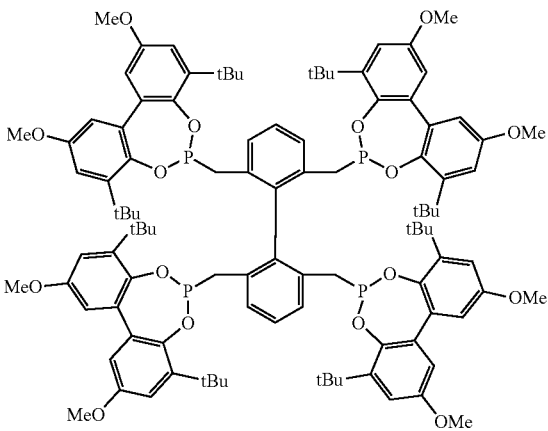

L90

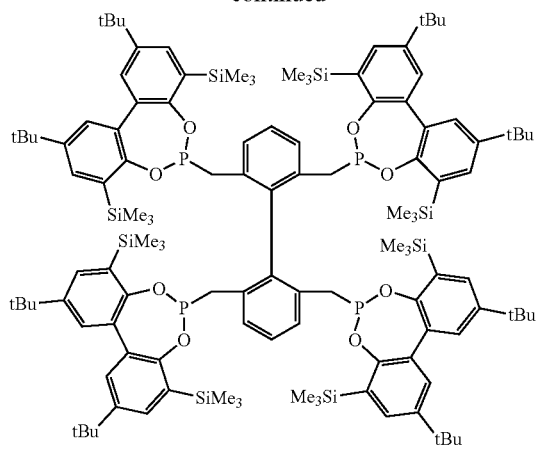

L91

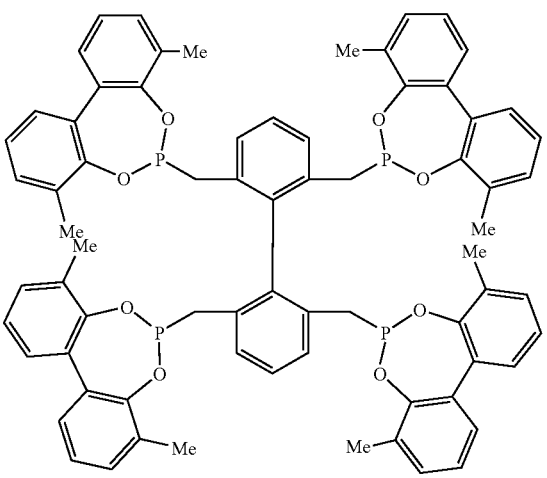

In a hydroformylation or related reaction, the transition metal-tetraphosphorous ligand complex is prepared by mixing a transition metal salt with the ligand. The transition metal salt is a salt of a transition metal selected from the group consisting of Fe, Zn, Mn, Co, Cu, Ag, Ni, Pt, Pd, Rh, Ru and Ir. Examples of the transition metal salts are $FeX_3$, $Fe(OTf)_3$, $Fe(OAc)_3$, $Mn(OAc)_3$, $Mn(OTf)_3$, $MnX_3$, $Zn(OTf)_2$, $Co(OAc)_2$, $AgX$, $Ag(OTf)$, $Ag(OTf)_2$, $AgOAc$, $PtCl_2$, $H_2PtCl_4$, $Pd_2(DBA)_3$, $Pd(OAc)_2$, $PdCl_2(RCN)_2$, $(Pd(allyl)Cl)_2$, $Pd(PR_3)_4$, $(Rh(NBD)_2)X$, $(Rh(NBD)Cl)_2$, $(Rh(COD)Cl)_2$, $(Rh(COD)_2)X$, $Rh(acac)(CO)_2$, $Rh(ethylene)_2(acac)$, $(Rh(ethylene)_2Cl)_2$, $RhCl(PPh_3)_3$, $Rh(CO)_2Cl_2$, $RuH(CO)_2(PPh_3)_2$, $Ru(Ar)X_2$, $Ru(Ar)X_2(PPh_3)_3$, $Ru(COD)(COT)$, $Ru(COD)(COT)X$, $RuX_2(cymen)$, $Ru(COD)_n$, $RuCl_2(COD)$, $(Ru(COD)_2)X$, $RuX_2(PN)$, $RuCl_2(=CHR)(PR'_3)_2$, $Ru(ArH)Cl_2$, $Ru(COD)(methallyl)_2$, $(Ir(NBD)_2Cl)_2$, $(Ir(NBD)_2)X$, $(Ir(COD)_2Cl)_2$, $(Ir(COD)_2)X$, $CuX(NCCH_3)_4$, $Cu(OTf)$, $Cu(OTf)_2$, $Cu(Ar)X$, $CuX$, $Ni(acac)_2$, $NiX_2$, $(Ni(allyl)X)_2$, $Ni(COD)_2$, $MoO_2(acac)_2$, $Ti(OiPr)_4$, $VO(acac)_2$ and $MeReO_3$, wherein each R and R' is independently selected from the group consisting of alkyl or aryl; Ar is an aryl group; X is a counteranion, such as $BF_4$, $ClO_4$, $OTf$, $SbF_6$, $CF_3SO_3$, $B(C_6H_3(CP_3)_2)_4$, Cl, Br or I; OTf is $OSO_2CF_3$; DBA is PhCH=CHCOCH=CHPh, NDB is norbornadiene; COD is cyclooctodiene and COT is cyclooctotriene. The mixture is placed in an autoclave that is purged with nitrogen and subsequently charged with CO and $H_2$.

Synthesis of the Tetraphosphate Ligand

All reactions and manipulations in the example set forth below were performed in a nitrogen-filled glovebox or using standard Schlenk techniques. THF and toluene were dried and distilled from sodium-benzophenone ketyl under nitrogen. Methylene chloride was distilled from $CaH_2$. Methanol was distilled from Mg under nitrogen. Column chromatography was performed using EM silica gel 60 (230–400 mesh). 1H, 13C and 31P NMR were recorded on Bruker WP-200, AM-300, and AMX-360 spectrometers. Chemical shifts were reported in ppm down field from tetramethylsilane with the solvent resonance as the internal standard. MS spectra were recorded on a KRATOS mass spectrometer MS 9/50 for LR-EI and HR-EI. GC analysis was carried on Helwett-Packard 6890 gas chromatography using chiral capillary columns. HPLC analysis was carried on Waters™ 600 chromatography.

The following procedure was used to synthesize ligand having the structure LI. To a solution of chlorodipyrrolyphosphine (4.4 mmol, 0.87 g) in THF (10 mL) was added dropwise triethylamine 1 mL and a solution of tetraol (1 mmol, 0.218 g) in THF (5 mL) at room temperature. Tetraol was synthesized according to Lindsten, G.; Wennerstroem, O.; Isaksson, R., *J. Org. Chem.* 1987, 52, 547-54, and chlorodipyrrolyphosphine was prepared according van der Slot, S. C.; Duran, J.; Luten, J.; Kamer, P. C. J.; van Leeuwen, P. W. N. M. *Organometallics* 2002, 21, 3873-3883. Triethylamine•HCl salts were formed immediately after the addition. The reaction mixture was stirred for 6 h at room temperature. The triethylamine•HCl salts were then filtered off and the solvent was removed under vacuum. The crude product was purified by flash chromatography on basic aluminum oxide eluted with hexane/EtOAc/$NEt_3$ (6:1:0.01) to produce ligand L1 (0.31 g, 36%) as a air-stable colorless solid. $^1$H NMR (300 Hz, $CDCl_2$), δ 7.23 (t, 2H, J=8.3 Hz), 6.68 (m, 20H), 6.21 (m, 16H); $^{13}$C NMR (90 Hz, $CDCl_2$), δ 152.86 (d, J=12.2 Hz 131.0, 121.4 (d, J=16.8 Hz), 118.1, 115.3 (d, J=13.7 Hz), 112.7; 31P NMR (146 Hz, $CDCl_2$), δ 107.3. HRMS (ES$^+$), calcd. for $C_{44}H_{39}N_8O_4P_4$ [MH$^+$] 867.2045, found 867.2021.

Typical Hydroformylation Process

To a 2 mL vial with a magnetic stirring bar was charged the tetraphosphorus ligand L1 prepared in the previous example (3 μmol, 2.6 mg) and Rh(acac)(CO)$_2$ (1 μmol, 0.1 mL of 10 mM solution in toluene). The mixture was stirred for 5 min. Then 2-octene (10 mmol, 1.56 mL) was added followed by decane (0.01 mL) as internal standard. The reaction mixture was transferred to an autoclave. The autoclave was purged with nitrogen for three times and subsequently charged with CO (5 bar) and H$_2$ (5 bar). The autoclave was then heated to 100° C. (oil bath). After 12 h, the autoclave was cooled in icy water and the pressure was carefully released in a well ventilated hood. The reaction mixture was immediately analyzed by GC.

The remarkable regioselectivities using a multi-chelating tetraphosphorus ligand L1 for hydroformylation of styrene, 1-octene and 1-hexene are demonstrated in Table 1. Normally, styrene is a difficult substrate for achieving more than 2:1 ratio of linear to branched products when compared to bisphosphorous ligands of the prior art such as xantphos and UC-44. As shown in Table 1, the new tetraphosphorus ligands (Type A) such as L1 is more selective hydroformylation ligand than the prior art bisphosphorous ligand (Type B). The reaction conditions included 0.1 mol % Rh(CO)$_2$(acac) and ligand, reaction temperature 80° C. for 1 hour at 20 atm of CO and H$_2$. These results indicate that tetraphosphorus ligands with multi-chelating coordination can be used to increase coordinating abilities of bisphosphine ligands. The regioselectivity with Type A is the highest reported to date.

TABLE 1

| Regioselective Hydroformulation of Alkenes | | | |
|---|---|---|---|
| | Linear vs Branched ratio | | |
| Ligand | Styrene | 1-octene | 1-hexene |
| | 5:1 | 372:1 | 382:1 |

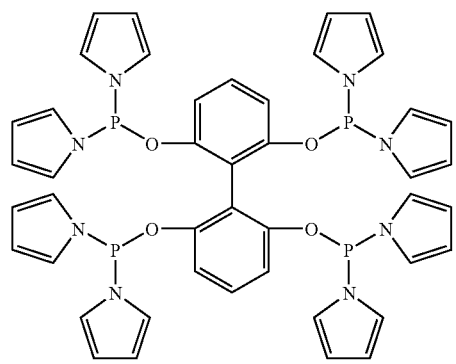

Type A (L1)

TABLE 1-continued

Regioselective Hydroformulation of Alkenes

| Ligand | Linear vs Branched ratio | | |
|---|---|---|---|
| | Styrene | 1-octene | 1-hexene |
| Type B | 1.5:1 | 74:1 | 81:1 |

The results of hydroformylation of 2-hexene and 2-octene using the tetraphosphorus ligand (Type A) vs bisphosphorus ligand (Type B) to produce an aldehyde are summarized below in Table 2. In Tables 2 to 11 which follow, "n:i" is the ratio of linear aldehyde to branched aldehyde and "TOF" is turnover frequency (turnover per catalyst per hour). The tetraphosphorus ligands of the present invention produce higher "n:i" ratios than bisphosphorus ligands.

Rh ratio is 3:1, reaction temperature is 100° C., $CO/H_2$ is 5/5 atm, toluene is the solvent, and decane is the internal standard.

Table 3 below shows the results of hydroformylation of 1-hexene and 1-octene using the tetraphosphorus ligand (Type A) vs bisphosphorus ligand (Type B) to produce an aldehyde by a hydroformylation reaction.

TABLE 3

Results of Hydroformylation of 1-Hexene and 1-Octene

| Substrate | Ligand | Time (h) | Yield of Aldehyde | n:i | Linear Selectivity | TOF $(mol \cdot h)^{-1}$ | Isomerization |
|---|---|---|---|---|---|---|---|
| 1-hexene | tetraphos | 1 | 67.2% | 382 | 99.7% | $6.7 \times 10^3$ | 18.7% |
| 1-hexene | tetraphos | 2 | 80.4% | 380 | 99.7% | $4.0 \times 10^3$ | 18.4% |
| 1-hexene | bisphos | 1 | 79.3% | 80.8 | 98.8% | $7.9 \times 10^3$ | 12.2% |
| 1-hexene | bisphos | 2 | 87.2% | 78.1 | 98.7% | $4.4 \times 10^3$ | 12.4% |
| 1-octene | tetraphos | 1 | 68.6% | 372 | 99.7% | $6.9 \times 10^3$ | 15.3% |
| 1-octene | tetraphos | 2 | 83.6% | 369 | 99.7% | $4.2 \times 10^3$ | 15.1% |
| 1-octene | bisphos | 1 | 83.9% | 74.1 | 98.7% | $8.4 \times 10^3$ | 10% |
| 1-octene | bisphos | 2 | 88.6% | 69.4 | 98.6% | $4.4 \times 10^3$ | 10.7% |

TABLE 2

Results of Hydroformylation of 2-Hexene and 2-Octene

| Substrate | Ligand | Time (h) | Yield of Aldehyde | n:i | Linear Selectivity | TOF $(mol \cdot h)^{-1}$ |
|---|---|---|---|---|---|---|
| 2-hexene | tetraphos | 1 | 17.0% | 80.6 | 98.8% | $1.7 \times 10^3$ |
| 2-hexene | tetraphos | 12 | 59.9% | 56 | 98.2% | $0.50 \times 10^3$ |
| 2-hexene | bisphos | 1 | 20.7% | 15 | 93.8% | $2.1 \times 10^3$ |
| 2-hexene | bisphos | 12 | 68.2% | 13.5 | 93.1% | $0.57 \times 10^3$ |
| 2-octene | tetraphos | 1 | 15.1% | 51.7 | 98.1% | $1.5 \times 10^3$ |
| 2-octene | tetraphos | 12 | 77.2% | 38 | 97.4% | $0.64 \times 10^3$ |
| 2-octene | bisphos | 1 | 23.0% | 10.1 | 91% | $2.3 \times 10^3$ |
| 2-octene | bisphos | 12 | 84.3% | 5.5 | 84.6% | $0.70 \times 10^3$ |

The hydroformylation conditions were S/C=10000, [Rh] is 0.69 mM (for 2-hexene) and 0.57 mM (for 2-octene), Ligand/

The reaction conditions: S/C=10000, Rh concentration is 0.2 mM, Ligand/Rh ratio is 3:1, temperature is 80° C., $CO/H_2$ is 10/10 atm, toluene is the solvent, and decane is the internal standard.

The hydroformylation reaction is highly dependent on the reaction conditions. Typical reaction conditions are S/C=10000, ligand metal ratio of about 3, transition metal concentration of about 0.2 to 0.7 mM, reaction temperature is 100° C., and the reaction time is 12 h. To optimize the reaction conditions, the following experiments have been carried out with tetraphosphorus ligand (L1). As evidenced by the "n:i" ratios in Tables 2 and 3, there a substantial and significant improvement in the amount of linear aldehyde produced using a tetraphosphorus ligand of the present invention as opposed to using a bisphosphorus ligand.

Ligand to Metal Ratio

The hydroformylation was first carried out with different ligand to metal ratios. As shown in Table 4, increasing the ligand metal ratio slightly decreased the reaction rate. On the other hand, the ligand to metal ratio significantly affects the regioselectivity. At lower ratios, low regioselectivity were observed. A minimum ligand to metal ratio of 2 is essential to achieve high regioselectivity, which allows the tetraphosphorus ligand to be coordinated in a multi-coordination mode. Further increasing the ligand to metal ratio did not significantly improve the regioselectivity.

TABLE 4 hydroformylation of 2-octene with different ligand metal ratio using ligand L1.

| L/Rh ratio | n:i | Linear Selectivity | TOF[$h^{-1}$] |
|---|---|---|---|
| 1:2 | 2.92 | 74.5% | $2.1 \times 10^3$ |
| 1:1 | 17.7 | 94.7% | $1.8 \times 10^3$ |
| 2:1 | 43.4 | 97.7% | $1.5 \times 10^3$ |
| 4:1 | 46 | 97.9% | $1.5 \times 10^3$ |

The reaction conditions: substrate is 2-octene, S/C=10000, Rh concentration is 0.57 mM, temperature is 100° C., $CO/H_2$ is 10/10 atm, reaction time is 1 h, toluene is the solvent, and decane is the internal standard. The results in Table 4 show that presence of two of free phosphorus ligands with the tetraphosphorus ligand is important for achieving high regioselectivity (n:i goes from 2.92 to 17.7). Table 5 below shows similar results with 2-hexene as the substrate.

TABLE 5

Hydroformylation of 2-hexene with different ligand metal ratio using ligand L1.

| L/Rh ratio | n:i | Linear Selectivity | TOF[$h^{-1}$] |
|---|---|---|---|
| 1:2 | 12.7 | 92.7% | $2.2 \times 10^3$ |
| 1:1 | 42 | 97.7% | $1.9 \times 10^3$ |
| 2:1 | 68.5 | 98.6% | $1.9 \times 10^3$ |
| 4:1 | 70.3 | 98.6% | $1.8 \times 10^3$ |

Reaction conditions: substrate is 2-hexene, S/C=10000, Rh concentation is 0.69 mM, reaction temperature is 100° C., $CO/H_2$ is 10/10 atm, reaction time is 1 h, toluene is the solvent, and decane is the internal standard. The results in Table 5 show that presence of two of free phosphorus ligands with the tetraphosphorus ligand is important for achieving high regioselectivity (n:i goes from 12.7 to 42).

Temperature

The reaction temperature also plays a key role in hydroformylation. As shown in Tables 6 and 7 below, at low temperature, though high regioselectivity was observed, the reaction rate was low. To facilitate the olefin isomerization and hydroformylation, high temperature (100° C.) is preferred to achieve high reaction rate as well as acceptable regioselectivity.

TABLE 6

Hydroformylation of 2-octene at different temperature using a Rh-ligand L1

| T° C. | n:i | Linear Selectivity | TOF[$h^{-1}$] |
|---|---|---|---|
| 140 | 29.5 | 96.7% | $3.7 \times 10^3$ |
| 120 | 30.4 | 96.8% | $3.4 \times 10^3$ |
| 100 | 46 | 97.9% | $1.6 \times 10^3$ |
| 80 | 47.7 | 97.9% | $0.77 \times 10^3$ |
| 60 | 53.6 | 98.2% | $0.14 \times 10^3$ |

Reaction conditions: substrate is 2-octene, S/C=10000, Rh concentration is 0.57 mM, Ligand/Rh ratio is 3:1, $CO/H_2$ is 10/10 atm, reaction time is 1 h, toluene is the solvent, and decane s the internal standard.

TABLE 7

Hydroformylation of 2-hexene at different temperature using Rh-ligand L1

| T° C. | n:i | Linear Selectivity | TOF[$h^{-1}$] |
|---|---|---|---|
| 140 | 24.3 | 96% | $4.4 \times 10^3$ |
| 120 | 49.5 | 98% | $2.8 \times 10^3$ |
| 100 | 68.1 | 98.6% | $1.7 \times 10^3$ |
| 80 | 114 | 99.1% | $0.99 \times 10^3$ |
| 60 | 179 | 99.4% | $0.67 \times 10^3$ |

Reaction conditions: substrate is 2-hexene, S/C=10000, Rh concentration is 0.69 mM, Ligand/Rh ratio is 3:1, $CO/H_2$ is 10/10 atm, reaction time is 1 h, toluene is the solvent, and decane is the internal standard.

Pressure

The CO/H2 total pressure also influences the reaction. At high pressure, both reaction rate and regioselectivity were low. Lowering the pressure generally results in higher reaction rate and regioselectivity. Decreasing the $CO/H_2$ pressure from 10/10 atm to 5/5 atm did not change the reaction rate very much, but the regioselectivity improved further. The results from the hydroformylation of 2-octene and 2-hexene are shown in Tables 8 and 9.

TABLE 8

Hydroformylation of 2-octene at different pressure using ligand L1

| $CO/H_2$ Pressure | n:i | Linear Selectivity | TOF[$h^{-1}$] |
|---|---|---|---|
| 30/30 atm | 24.3 | 96% | $0.31 \times 10^3$ |
| 20/20 atm | 30 | 96.8% | $0.51 \times 10^3$ |
| 10/10 atm | 46 | 98% | $1.6 \times 10^3$ |
| 5/5 atm | 51.7 | 98.1% | $1.5 \times 10^3$ |

Reaction conditions: substrate is 2-octene, S/C=10000, Rh concentration is 0.57 mM, Ligand/Rh ratio is 3:1, reaction temperature is 100° C., reaction time is 1 h, toluene is the solvent, and decane is the internal standard.

TABLE 9

Hydroformylation 2-hexene at different pressure using ligand L1

| CO/H$_2$ Pressure | n:i | Linear Selectivity | TOF[h$^{-1}$] |
|---|---|---|---|
| 30/30 atm | 54.8 | 98.2% | 0.96 × 10$^3$ |
| 20/20 atm | 58.8 | 98.3% | 1.3 × 10$^3$ |
| 10/10 atm | 68.1 | 98.6% | 1.7 × 10$^3$ |
| 5/5 atm | 80.6 | 98.8% | 1.7 × 10$^3$ |

Reaction conditions: substrate is 2-hexene, S/C=10000, Rh concentration is 0.69mM, Ligand/Rh ratio is 3:1, reaction temperature is 100° C., reaction time is 1 h, toluene is the solvent, and decane is the internal standard.

Reaction Time

The reaction time also affects the hydroformylation selectivity. As shown in Tables 10 and 11 below, the longer the reaction time, the lower the regioselectivity. Further an increase in the reaction time from 12 h to 18 h only slightly improved the turnover number (TON), i.e. turnover per catalyst, at the expense of decreased regioselectivity.

TABLE 10

Hydroformylation of 2-octene at different time using ligand L1

| Time (h) | n:i | Linear Selectivity | TON | TOF (h$^{-1}$) |
|---|---|---|---|---|
| 1 | 51.7 | 98.1% | 1.5 × 10$^3$ | 1.5 × 10$^3$ |
| 2 | 51.3 | 98.1% | 2.8 × 10$^3$ | 1.4 × 10$^3$ |
| 6 | 41.3 | 97.6% | 5.7 × 10$^3$ | 0.94 × 10$^3$ |
| 12 | 38 | 97.4% | 7.7 × 10$^3$ | 0.64 × 10$^3$ |
| 18 | 27.7 | 96.5% | 8.1 × 10$^3$ | 0.45 × 10$^3$ |

Reaction conditions: substrate is 2-octene, S/C=10000, Rh concentration is 0.57 mM, Ligand/Rh ratio is 3:1, reaction temperature is 100° C., CO/H$_2$ is 5/5 atm, toluene is the solvent, and decane is the internal standard.

TABLE 11

Hydroformylation of 2-hexene at different time using ligand L1

| Time (h) | n:i | Linear Selectivity | TON | TOF (h$^{-1}$) |
|---|---|---|---|---|
| 1 | 80.6 | 98.8% | 1.7 × 10$^3$ | 1.7 × 10$^3$ |
| 2 | 71.9 | 98.6% | 2.4 × 10$^3$ | 1.2 × 10$^3$ |
| 6 | 63 | 98.4% | 5.5 × 10$^3$ | 0.92 × 10$^3$ |
| 12 | 56 | 98.2% | 6.0 × 10$^3$ | 0.5 × 10$^3$ |
| 18 | 51.9 | 98.1% | 6.7 × 10$^3$ | 0.37 × 10$^3$ |

Reaction conditions: substrate is 2-hexene, S/C=10000, Rh concentration is 0.69 mM, Ligand/Rh ratio is 3:1, reaction temperature is 100° C., CO/H$_2$ is 5/5 atm, toluene is the solvent, and decane is the internal standard.

While this invention has been described with reference to several preferred embodiments, it is contemplated that various alterations and modifications thereof will become apparent to those skilled in the art upon a reading of the preceding detailed description. It is therefore intended that the following appended claims be interpreted as including all such alterations and modifications as fall within the true spirit and scope of this invention.

What is claimed is:

1. A phosphorous ligand having the following formula:

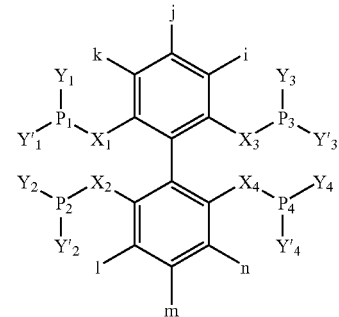

wherein i, j, k, l, m and n are, independently, H, R, Ar, substituted Ar, OR, OAr, COOEt, halide, SO$_2$R, SO$_3$H, SO$_2$NHR, POR$_2$, POAr$_2$ or NR$_2$, where R is an alkyl, substituted alkyl, aryl or substituted aryl and Ar is an aryl; X$_1$-X$_4$ are, independently, O, or CH$_2$; and Y$_1$, Y'$_1$, Y$_2$, Y'$_2$, Y$_3$, Y'$_3$, Y$_4$, Y'$_4$, are, independently, R, Ar, OR, OAr, pyrrole or substituted pyrrole, or where R, Ar, OR, OAr, pyrrole and substituted pyrrole are linked with a carbon to carbon bond, CH$_2$, NH, NR or O.

2. The phosphorous ligand according to claim 1, wherein the ligand has the following structure:

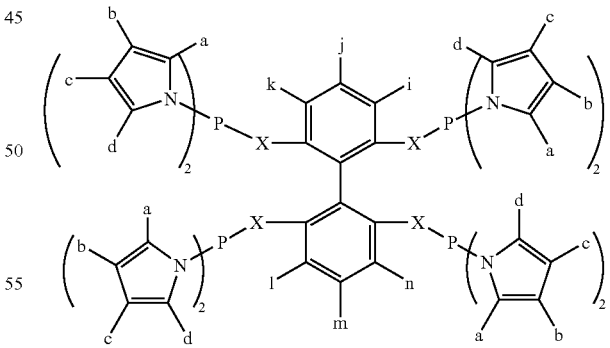

wherein X is O, or CH$_2$; and a, b c d, i,j, k, l, m and n are, independently, H, alkyl, aryl, substituted alkyl, substituted aryl, OR, OAr, SiR$_3$, CF$_3$, COOR, SO$_3$R, SO$_3$H, POR$_2$, halide or two of a, b, c, d, i, j, k, l, m and n can be a cyclic fused ring or an extended aromatic ring.

3. The phosphorous ligand according to claim 1, wherein the ligand has the following structure:

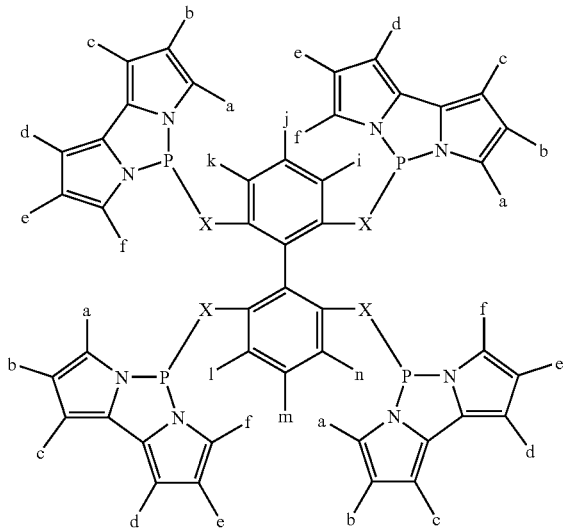

wherein X is O, or CH$_2$; and a, b, c, d, e, f, i, j, k, l, m and n are, independently, H, alkyl, aryl, substituted alkyl, substituted aryl, OR, OAr, SiR$_3$, COOR, SO$_3$R, SO$_3$H, POR$_2$, halide or two of a, b, c, d, e, f, i, j, k, l, m and n can be a cyclic fused ring or an extended aromatic ring.

4. The phosphorous ligand according to claim 1, wherein the ligand has the following structure:

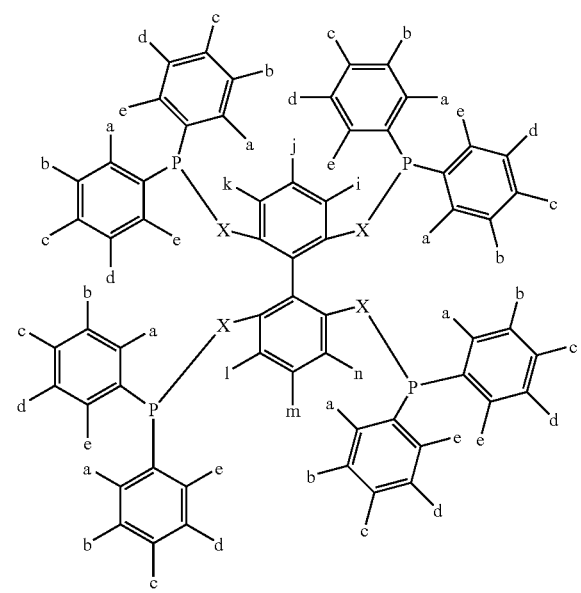

wherein X is O, or CH$_2$; and a, b, c, d, e, i, j, k, l, m and n are, independently, H, alkyl, aryl, substituted alkyl, substituted aryl, OR, OAr, SiR$_3$, CF$_3$, COOR, SO$_3$R, SO$_3$H, POR$_2$, halide, NR$_2$, or two of a, b, c, d, e, i, j, k, l, m and n can be a cyclic fused ring or an extended aromatic ring.

5. The phosphorous ligand according to claim 1, wherein the ligand has the following structure:

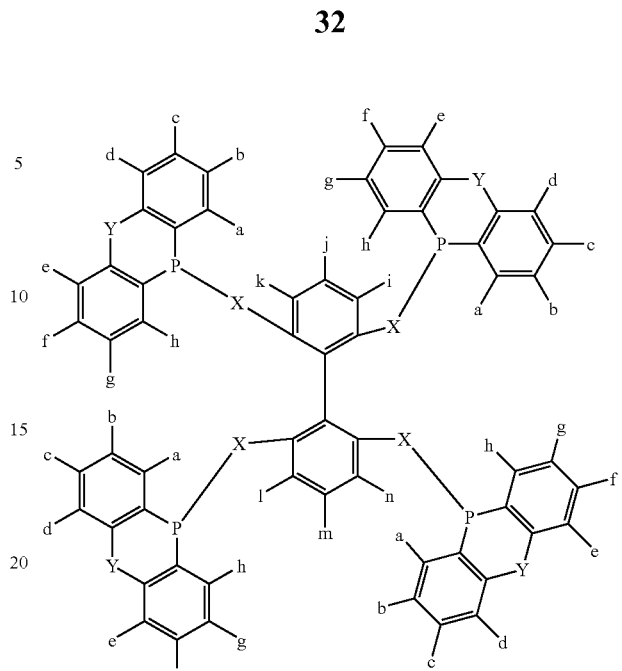

wherein X is O, or CH$_2$; Y is a carbon-carbon bond, O, CH$_2$, NH or NR, where R is an alkyl, substituted alkyl, aryl or substituted aryl; and a to n are, independently, H, alkyl, aryl, substituted alkyl, substituted aryl, OR, OAr, SiR$_3$, CF$_3$, COOR, SO$_3$R, SO$_3$H, POR$_2$, halide, NR$_2$, or two of a to n can be a cyclic fused ring or an extended aromatic ring.

6. The phosphorous ligand according to claim 1, wherein the ligand has the following structure:

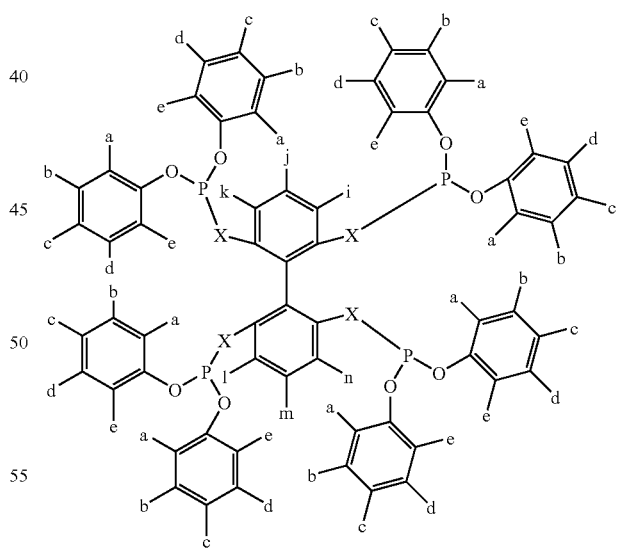

wherein X is O, or CH$_2$; and a, b, c, d, e, i, j, k, l, m and n are, independently, H, alkyl, aryl, substituted alkyl, substituted aryl, OR, OAr, SiR$_3$, CF$_3$, COOR, SO$_3$R, SO$_3$H, POR$_2$, halide, NR$_2$, or two of a, b, c, d, e, i, j, k, l, m and n can be a cyclic fused ring or an extended aromatic ring.

7. The phosphorous ligand according to claim 1, wherein the ligand has the following structure:

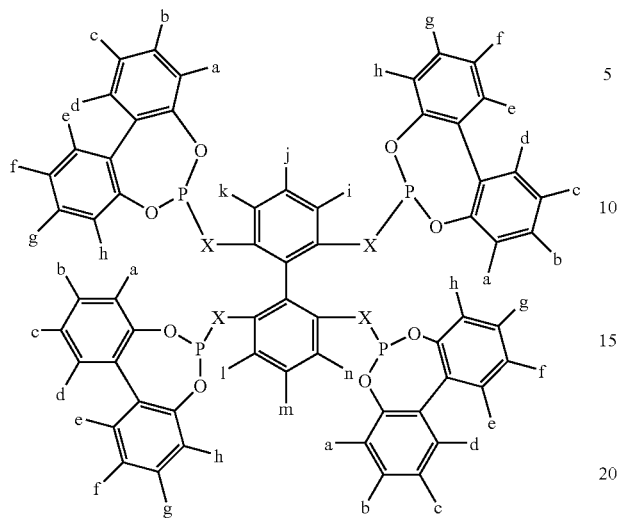
wherein X is O, or CH$_2$; and a to n are, independently, H, alkyl, aryl, substituted alkyl, substituted aryl, OR, OAr, SiR$_3$, CF$_3$, COOR, SO$_3$R, SO$_3$H, POR$_2$, halide, NR$_2$, or two of a to n can be a cyclic fused ring or an extended aromatic ring.
8. The phosphorous ligand according to claim 1, wherein the ligand has the following structure:
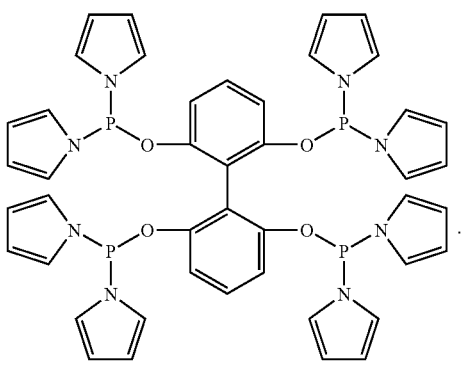
* * * * *

UNITED STATES PATENT AND TRADEMARK OFFICE
CERTIFICATE OF CORRECTION

| | | |
|---|---|---|
| PATENT NO. | : 7,531,698 B2 | Page 1 of 1 |
| APPLICATION NO. | : 11/639438 | |
| DATED | : May 12, 2009 | |
| INVENTOR(S) | : Xumu Zhang et al. | |

It is certified that error appears in the above-identified patent and that said Letters Patent is hereby corrected as shown below:

COLUMN 1, LINE 4-7, insert:

--<u>Government Interest in the Invention</u>

This invention was made with government support under Grant No. R01-GM058832, awarded by the National Institutes of Health. The Government has certain rights in the invention.--.

Signed and Sealed this

First Day of September, 2009

David J. Kappos
*Director of the United States Patent and Trademark Office*